US012693286B2

(12) United States Patent
Clarke et al.

(10) Patent No.: US 12,693,286 B2
(45) Date of Patent: Jul. 28, 2026

(54) DRILLING FLUID OPTIMIZATION FOR CUTTINGS TRANSPORT AND RATE OF PENETRATION

(71) Applicant: Schlumberger Technology Corporation, Sugar Land, TX (US)

(72) Inventors: Andrew Clarke, Cambridge (GB); Mahdi Davoodi, Cambridge (GB); John Morrison Whyte, Cambridge (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 376 days.

(21) Appl. No.: 18/462,693

(22) Filed: Sep. 7, 2023

(65) Prior Publication Data

US 2025/0085268 A1     Mar. 13, 2025

(51) Int. Cl.
| | |
|---|---|
| *G01N 33/28* | (2006.01) |
| *E21B 21/06* | (2006.01) |
| *E21B 21/08* | (2006.01) |
| *E21B 47/08* | (2012.01) |

(52) U.S. Cl.
CPC ....... *G01N 33/2823* (2013.01); *E21B 21/068* (2013.01); *E21B 21/08* (2013.01); *E21B 47/08* (2013.01)

(58) Field of Classification Search
None
See application file for complete search history.

(56) References Cited

U.S. PATENT DOCUMENTS

| | | | | |
|---|---|---|---|---|
| 2013/0332089 | A1* | 12/2013 | Kulkarni | G01N 11/00 |
| | | | | 702/50 |
| 2022/0186604 | A1* | 6/2022 | Hammond | E21B 49/005 |

OTHER PUBLICATIONS

Coussot et al, "Rheophysical classification of concentrated suspensions and granular pastes," 1999, Physical Review E, vol. 59, No. 4, pp. 4445-4457 (Year: 1999).*
Busch et al., "Cuttings transport modeling—part 2: dimensional analysis and scaling," 2020, SPE Drilling & Completion, vol. 35, No. 01, pp. 69-87 (Year: 2020).*

(Continued)

*Primary Examiner* — Ivan R Goldberg
(74) *Attorney, Agent, or Firm* — Jeffrey D. Frantz

(57) ABSTRACT

Methods and systems are provided that determine at least one fluid parameter for a drilling fluid and a particular drilling operation, wherein the at least one fluid parameter is selected from the group consisting of: i) a first fluid parameter that relates to shear forces that break apart components of the drilling fluid during the particular drilling operation, ii) a second fluid parameter that characterizes mixing of drill cuttings with the drilling fluid during the particular drilling operation, and iii) third and fourth fluid parameters that characterize normal stress in the drilling fluid during the drilling operation. The methods and systems can evaluate one or more of these fluid parameters to determine a drilling fluid formulation that optimizes the drilling fluid for effective transport of drill cuttings. Methods and systems are also provided that evaluate one or more of these fluid parameters to determine operating parameters that optimize a drilling operation for effective transport of drill cuttings using the drilling fluid.

12 Claims, 9 Drawing Sheets

(56) References Cited

OTHER PUBLICATIONS

Wang, "Lubricity and Rheological Properties of Highly Dispersed Graphite in Clay-Water-Based Drilling Fluids," 2022, Materials, vol. 15, 1083, pp. 1-13 (Year: 2022).*

Kang, "Flow instability and transitions in Taylor-Couette flow of a semidilute non-colloidal suspension," 2021, Journal of Fluid Mechanics, vol. 916, A12, pp. 1-27 (Year: 2021).*

Khajehesamedini, "Hybrid Modeling of the Electrocoalescence Process in Water-in-Oil Emulsions," 2018, Energy Fluids, vol. 32, pp. 5596-5610 (Year: 2018).*

Hashemian, et al. "Experimental study and modelling of barite sag in annular flow," 2014, Journal of Canadian Petroleum Technology, 53(06), pp. 365-374 (Year: 2014).*

Vickers et al., "Enhanced Hole Cleaning and Suspension with Reduced Rheology", AADE Fluids Technical Conference and Exhibition, Houston, 2020, 10 pages.

Koumakis et al., "Tuning colloidal gels by shear", Soft Matter, The Royal Society of Chemistry, 2015, 11, pp. 4640-4648.

Clarke, "Gel breakdown in a formulated product via accumulated strain", Soft Matter, 2021, 17, pp. 7893-7902.

Tran et al., "The relaxation time of entangled HPAM solutions in flow", Journal of Non-Newtonian Fluid Mechanics, Jan. 2023, vol. 311, 104954, 7 pages.

Poole, "Measuring normal-stresses in torsional rheometers: a practical guide", The British Society of Rheology, Rheology Bulletin, 57(2), Aug. 2016, pp. 36-46.

Maklad et al., "A review of the second normal-stress difference; its importance in various flows, measurement techniques, results for various complex fluids and theoretical predictions", Journal of Non-Newtonian Fluid Mechanics, vol. 292(1), Mar. 2021, 68 pages.

IADC Drilling Manual, 12th edition, International Association of Drilling Contractors, USA, 2015, Chapters FP, HY and DP.

* cited by examiner

Figure 1A:
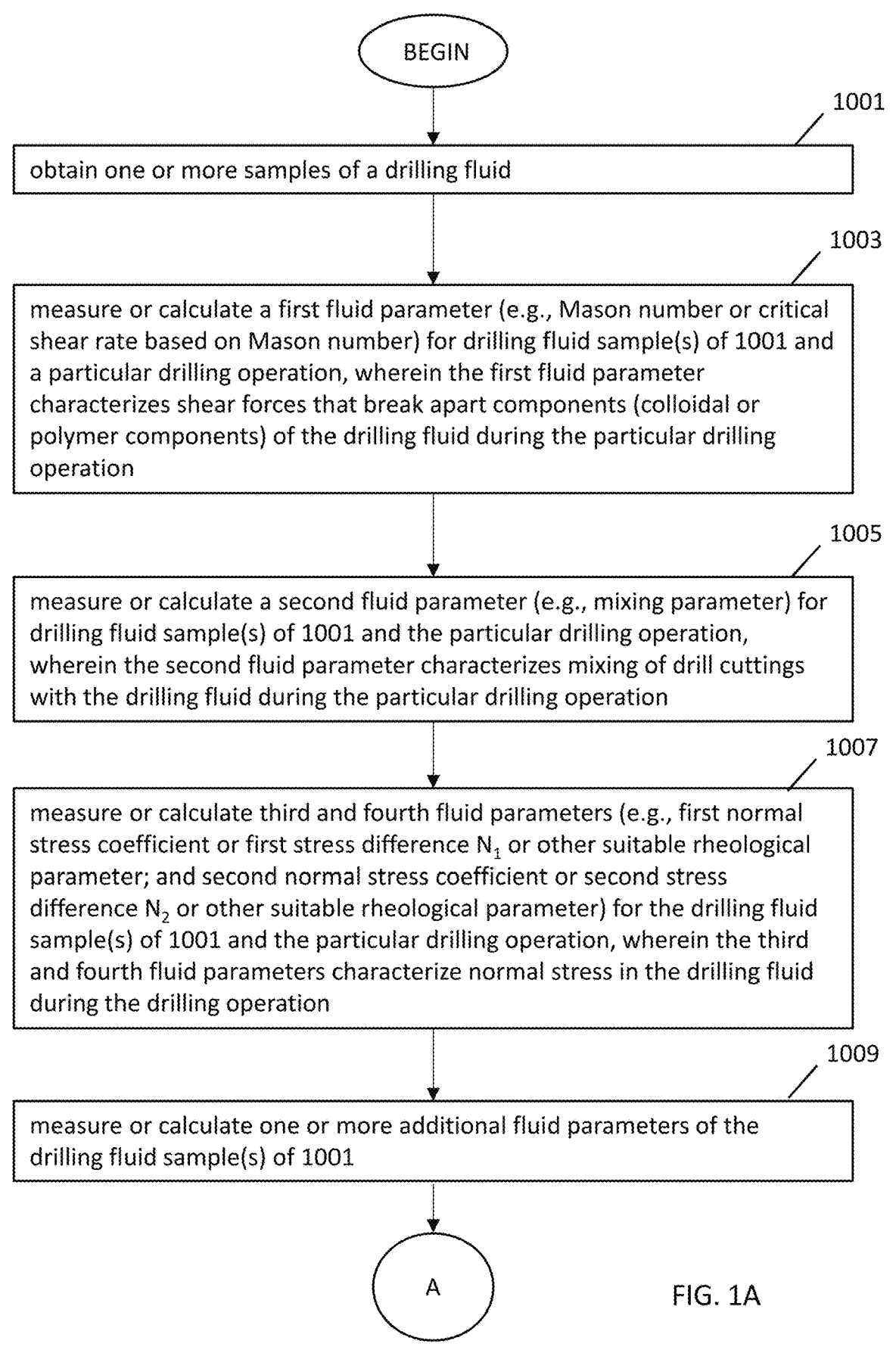

BEGIN

1001 obtain one or more samples of a drilling fluid

1003 measure or calculate a first fluid parameter (e.g., Mason number or critical shear rate based on Mason number) for drilling fluid sample(s) of 1001 and a particular drilling operation, wherein the first fluid parameter characterizes shear forces that break apart components (colloidal or polymer components) of the drilling fluid during the particular drilling operation

1005 measure or calculate a second fluid parameter (e.g., mixing parameter) for drilling fluid sample(s) of 1001 and the particular drilling operation, wherein the second fluid parameter characterizes mixing of drill cuttings with the drilling fluid during the particular drilling operation

1007 measure or calculate third and fourth fluid parameters (e.g., first normal stress coefficient or first stress difference $N_1$ or other suitable rheological parameter; and second normal stress coefficient or second stress difference $N_2$ or other suitable rheological parameter) for the drilling fluid sample(s) of 1001 and the particular drilling operation, wherein the third and fourth fluid parameters characterize normal stress in the drilling fluid during the drilling operation

1009 measure or calculate one or more additional fluid parameters of the drilling fluid sample(s) of 1001

FIG. 2A                                                    FIG. 2B measurement domain
of Couette device $$N_1(\dot{\gamma}) = \frac{2F_{CP}(\dot{\gamma})}{\pi R^2} = \tau_{xx} - \tau_{yy}$$

$$N_1(\dot{\gamma}) - N_2(\dot{\gamma}_R) = \frac{2F_{PP}(\dot{\gamma}_R)}{\pi R^2}\left(1 + \frac{1}{2}\frac{d\ln F_{PP}(\dot{\gamma}_R)}{d\ln \dot{\gamma}_R}\right)$$

1

DRILLING FLUID OPTIMIZATION FOR CUTTINGS TRANSPORT AND RATE OF PENETRATION

BACKGROUND

Boreholes, which are also commonly referred to as "well-bores" or "holes," are created for a variety of purposes, including exploratory drilling for locating underground deposits of different natural resources, mining operations for extracting such deposits, and construction projects for installing underground utilities. A common misconception is that all boreholes are vertically aligned with the drilling rig; however, many applications require the drilling of boreholes with vertically deviated and/or horizontal geometries. A well-known technique employed for drilling horizontal, vertically deviated, and other complex boreholes is directional drilling.

Directional drilling is generally defined as a process of boring a hole in the earth in a direction other than vertical (i.e., the axial direction of the borehole is oriented at an angle offset from the vertical direction, known as "vertical deviation").

Conventional directional drilling operates a device that pushes or steers a series of connected drill pipes with a directable drill bit at the distal end thereof to achieve the desired borehole geometry. In the exploration and recovery of subsurface hydrocarbon deposits, such as petroleum and natural gas, the directional borehole is typically drilled with a rotatable drill bit that is attached to one end of a bottom hole assembly or "BHA." A steerable BHA can include, for example, a positive displacement motor (PDM) or mud motor, drill collars, reamers, shocks, and under reaming tools to enlarge the wellbore. A stabilizer can be attached to the BHA to control the bending of the BHA to direct the drill bit in the desired direction (inclination and azimuth). The BHA, in turn, is attached to the bottom of a tubing assembly, often comprising jointed pipe or relatively flexible spoolable tubing, also known as "coiled tubing." This directional drilling system—i.e., the operatively interconnected tubing, drill bit and BHA, is usually referred to as a "drill string." When jointed pipe is utilized in the drill string, the drill bit can be rotated by rotating the jointed pipe from the surface, or through the operation of the mud motor contained in the BHA. In contrast, drill strings which employ coiled tubing generally rotate the drill bit via the mud motor in the BHA.

Drilling fluid, which is more commonly referred to as "mud," is often used to aid the drilling of boreholes into the earth, for example, to remove cuttings from the borehole, control formation pressure, and cool, lubricate and support the bit and drilling assembly. Typically, the drilling fluid is pumped down the borehole through the interior of the drill string and out through nozzles at the drill bit. In the region near the drill bit, the drilling fluid mixes with drill cuttings and the mixture flows upwardly in the well (typically in the annulus between the drill string and the wall of the borehole) to the surface.

During the ascent, some of the drilling fluid can form a cake on the exposed face of the wellbore. In addition, the pressure inside the formation can be partially or fully counterbalanced by the hydrostatic weight of the column of drilling fluid in the hole.

There are various types of drilling fluids, including: (1) water-based muds (WBM), which typically comprise a water-and-polymer based composition, (2) oil-based muds (OBM), where the base fluid is a petroleum product, such as diesel fuel, and (3) synthetic-based muds (SBM), where the base fluid is a synthetic oil. In many cases, oil-based muds can also have water or brine dispersed in the oil in significant proportions, and hydrophobically modified clay can be included as a viscosifier. While drilling a well, a water-based fluid can be used in one section of the borehole, while an oil-based fluid can be used in a different section of the borehole.

In the drilling operation, the rate of penetration (ROP) of the drill bit is limited by the ability of the drilling fluid to carry or transport drill cuttings away from the bottom hole assembly (BHA) in particular, and the wellbore in general. For example, if drilling produces drill cuttings faster than they can be carried away, the hole will jam. Thus, improving the ability of the drilling fluid to carry or transport drilling cuttings under a given set of conditions is equivalent to enabling, other constraints withstanding, a higher ROP for the drilling operation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Methods and systems are provided that determine at least one fluid parameter for a drilling fluid and a particular drilling operation, wherein the at least one fluid parameter is selected from the group consisting of: i) a first fluid parameter that relates to the shear forces that break apart components of the drilling fluid during the particular drilling operation, ii) a second fluid parameter that characterizes mixing of drill cuttings with the drilling fluid during the particular drilling operation, and iii) third and fourth fluid parameters that characterizes normal stress in the drilling fluid during the particular drilling operation. The particular drilling operation can be planned for use in an individual well or formation and tailored for that specific application. Alternatively, the particular drilling operation can be generalized for use in a certain type of well or formation and tailored for the more generalized application. The methods and systems can evaluate one or more of these fluid parameters to determine a drilling fluid formulation that optimizes the drilling fluid for effective transport of drill cuttings. Methods and systems are also provided that evaluate one or more of these fluid parameters to determine operating parameters that optimize a drilling operation for effective transport of drill cuttings using the drilling fluid.

In embodiments, the first fluid parameter can represent a Mason number, where the Mason number is based on a shear rate calculated from operating parameters of the particular drilling operation selected from the group consisting of: drill pipe outer radius, drilled borehole radius, angular velocity of the drill string/drill bit, and drilling fluid flow rate.

In embodiments, the first fluid parameter can represent a Mason number, or a critical shear rate based on a Mason number. In embodiments, the Mason number can be determined from shear rate and critical shear rate for the drilling fluid as $$Mn = \frac{\dot{\gamma}}{\dot{\gamma}_c}$$

3 with Mn being the Mason number, $\dot{\gamma}$ being the shear rate imposed on the drilling fluid by the drilling operations, and $\dot{\gamma}_c$ being a critical shear rate that, in one method, may be derived from the hysteresis observed in a measured flow curve.

In embodiments, the first fluid parameter can represent a Mason number calculated from a mathematical equation of the form $$Mn = \frac{12\pi\eta_0\phi^2 G_{10}}{\sigma_y^2}\left(\frac{\varepsilon}{r}\right)\dot{\gamma},$$

where Mn is the Mason number,
   $\eta_0$ is the fluid viscosity of the continuous phase in the drilling fluid,
   $\phi$ is the volume fraction of the dispersed phase in the drilling fluid,
   $G_{10}$ is the short time elastic modulus (at 10 second sample age) of the drilling fluid,
   $\sigma_y$ is the dynamic yield stress of the drilling fluid,
   $\varepsilon$ is the range of the interaction potential for the drilling fluid,
   r is the size of the dispersed-phase component in the drilling fluid, and
   $\dot{\gamma}$ is the shear rate imposed on the drilling fluid by the drilling operations.

In embodiments where the drilling fluid is a water-based mud, the first fluid parameter can represent a Mason number calculated from a mathematical equation of the form $$Mn = \frac{K\dot{\gamma}}{G},$$

where Mn is the Mason number,
   K is the plastic viscosity in the drilling fluid,
   G is the short time elastic modulus (at 10 second sample age) of the drilling fluid, and
   $\dot{\gamma}$ is the shear rate imposed on the drilling fluid by the drilling operations.

In embodiments where the drilling fluid is an oil-based mud, the first fluid parameter can represent a critical shear rate determined from flow curve measurements of the drilling fluid performed by an automated rheometer, wherein the flow curve measurements are configured according to operating parameters of the particular drilling operation selected from the group consisting of: drill pipe radius, drilled borehole radius, angular velocity of the drill string/drill bit, and drilling fluid flow rate. The flow curve measurements can be performed from high shear rate (1000 (1/s)) to low shear rate (e.g., 0.1 (1/s)) and then immediately increasing to 1000 (1/s). Other protocols can be used, e.g., inserting a waiting period after the lowest shear rate, or logarithmically increasing the time per point as the measurement proceeds to low shear rate. The purpose is to see hysteresis, which is a different curve going from high to low compared to going from low to high. The critical shear rate is then the boundary between where the two curves being apart at lower shear rates, overlay at higher shear rates.

In embodiments, the second fluid parameter can represent a dimensionless number based on the combination of a Froude number and a Shields number for the drilling fluid.

In embodiments, the dimensionless number can be calculated from a mathematical equation of the form:

4

$$\Xi = \left(\frac{\rho_f\omega R_i H}{n\eta}\sqrt{\frac{H}{R_i}} + 1\right)\frac{3}{2(\rho_s - \rho_f)ga}\eta\frac{R_i\omega}{H},$$

where $\Xi$ is the dimensional number based on the combination of a Froude number and a Shields number for the drilling fluid,
   $\rho_s$ is the characteristic density of the particles (drill cuttings),
   $\rho_f$ is the fluid density of the drilling fluid,
   a is the characteristic radius of the particles (drill cuttings),
   $R_i$ is the radius of the drilled borehole,
   $\omega$ is the angular velocity of the drill string/drill bit,
   $\eta$ is the viscosity of the drilling fluid at an appropriate shear rate,
   H is the gap between the drill pipe and the borehole ($H=R_i-R_o$),
   g is the gravitational constant, and
   n is an experimentally determined scale factor.

In embodiments, the dimensionless number $\Xi$ can be related to a mixing parameter, $\Lambda_M$, using a piecewise mathematical expression of the form:

$$\Lambda_M = \begin{cases} 0, & \Xi < 0.85 \\ 0.26\Xi - 0.221, & 0.85 \le \Xi \le 4 \\ 0.82, & \Xi > 4 \end{cases}$$

In embodiments, the third fluid parameter can represent a first normal stress coefficient $\Psi_1$, an $N_1$ stress difference, or another suitable rheological parameter of the drilling fluid; and the fourth fluid parameter can represent a second normal coefficient $\Psi_2$ of the drilling fluid, an $N_2$ stress difference, or another suitable rheological parameter of the drilling fluid. The first normal stress coefficient $\Psi_1$ is a function of the $N_1$ stress difference and shear rate. The second normal stress coefficient $\Psi_2$ is a function of the $N_2$ stress difference and shear rate. The $N_1$ stress difference and the $N_2$ stress difference can be measured using standard methodology as described in R. J. Poole, Measuring normal-stresses in torsional rheometers: a practical guide, BSR Bulletin, 57 (2016), and Maklad, R. J. Poole, A review of the second normal-stress difference; its importance in various flows, measurement techniques, results for various complex fluids and theoretical predictions, Journal of Non-Newtonian Fluid Mechanics, 292 (2021). The shear rate can be estimated. For example, a typical average shear rate in a well with rotation can be estimated as 100 $s^{-1}$.

In embodiments, the method and systems can further involve determining a transport efficiency metric based on the second fluid parameter in combination with a settling factor calculated from the first fluid parameter.

In embodiments, the settling factor can be calculated from equations of the form:

$$L^* = \frac{L}{h} = u_0\frac{9\eta(\dot{\gamma})d_a(M_n)}{2a^3(\rho_s - \rho_f)g},$$

$d_a=2(a+\delta)$, which may be approximated as, $$d_a = \begin{cases} \dfrac{2a}{Mn}, & Mn < 1 \\ 2a, & Mn \ge 1 \end{cases}$$

where $u_0$ is derived from operating parameters of the drilling operation, $\dot{\gamma}$ is derived from operating parameters of the drilling operation, $M_n$ is the Mason number for the drilling fluid and the drilling operation, a is the characteristic radius of the drilling cuttings, $\delta$ is an accreted gel thickness, $\rho_s$ is the density of the drill cuttings, $\rho_f$ is the fluid density of the drilling fluid, and g is the gravitational constant.

In embodiments, the transport efficiency metric can be determined from experiments that measure time taken to clear a fraction of particles from a measurement domain of a Couette device.

In other embodiments, the transport efficiency metric can be determined from experiments that measure flux of particles at an outlet of a Couette device over time.

In embodiments, the method and systems can further involve evaluating the transport efficiency metric to characterize transport of drill cuttings by the drilling fluid during the particular drilling operation for optimization of a drilling fluid formulation for the particular drilling operation.

In other embodiments, the method and systems can further involve evaluating the transport efficiency metric to characterize transport of drill cuttings by the drilling fluid during the particular drilling operation for optimization of one or more operating parameters for the particular drilling operation.

In embodiments, the method and systems can further involve evaluating at least one of the first parameter, the second parameter, and the third parameter with respect to predefined criteria to characterize transport of drill cuttings by the drilling fluid during the particular drilling operation for optimization of a drilling fluid formulation for the particular drilling operation.

In other embodiments, the method and systems can further involve evaluating at least one of the first parameter, the second parameter, and the third parameter with respect to predefined criteria to characterize transport of drill cuttings by the drilling fluid during the particular drilling operation for optimization of one or more operating parameters for the particular drilling operation.

In embodiments, the at least one fluid parameter can be determined by a data processor.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIGS. 1A and 1B, collectively, is a flowchart of a workflow that measures four fluid parameters for a drilling fluid and evaluates these fluid parameters in conjunction with other fluid parameters to determine a drilling fluid formulation that optimizes the drilling fluid for effective transport of drill cuttings in accordance with the present disclosure;

FIG. 2A is a schematic diagram of x-ray adsorption experiments performed on a sample of the drilling fluid in a rotating horizontal Couette device;

FIG. 2B is a schematic cross-sectional view diagram of the rotating horizontal Couette device of FIG. 2A and relevant parameters used in the experiments;

DETAILED DESCRIPTION

Figure 1B:
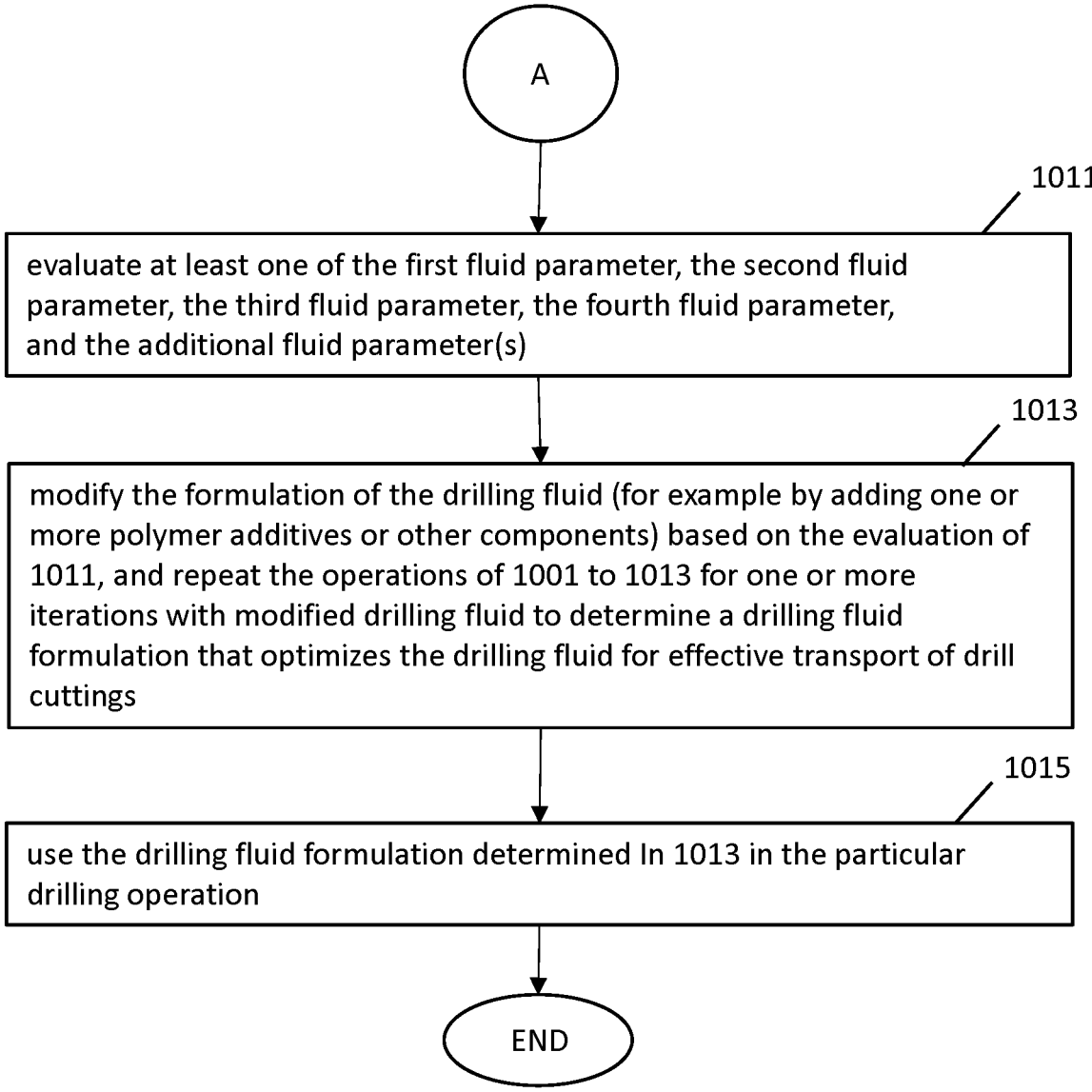

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

In the present disclosure, the transport of drill cuttings in drilling fluid is generally understood to be achieved by: (a) the drill cuttings being carried along by axial flow provided that the drill cuttings are suspended in the flow. If the drill cuttings sit as a bed on the lower side of the wellbore, then the drill cuttings move via saltation; and (b) the drill cuttings from the bed on the lower side of the wellbore mix with the drilling fluid such that the drill cuttings are suspended in the flow and hence may be carried by the axial flow.

It is commonly understood that the axial flow rate helps (a), and the rotation of the drill string helps (b). It is also commonly understood that the rheological parameter R6 (which represents shear stress of the drilling fluid at a Fann rheometer (R1B1 geometry) rotational speed of 6 rpm or 10.2 s$^{-1}$) is a useful characteristic to inform about transport of drill cuttings in that drilling fluid. Rules of thumb are set out in the IADC drilling manual, 12th edition, International Association of Drilling Contractors, USA, 2015.

Despite this understanding and the associated rules of thumb, there are reported instances that varying drilling cutting transport is provided by drilling fluids under the same measured fluid properties and the same drilling conditions. Thus, it is a logical conclusion that these drilling fluids in particular and all drilling fluids in general are not optimized for cuttings transport in their formulation. Furthermore, in operation it is unknown how to modify a drilling fluid to improve drill cuttings transport, without, for example, compromising equivalent circulating density. Equivalent circulating density, or ECD, is the effective density of the drilling fluid that exerts pressure on the formation while circulating. It depends on several factors, such as mud weight, flow rate, annular geometry, and friction losses. If ECD is too high, it can cause fracturing, lost circulation, or well control issues. If ECD is too low, it can result in hole collapse, stuck pipe, or influx.

The present disclosure provides methods and systems that measure one or more of four fluid parameters for a drilling fluid and connects these fluid parameters to the transport of drill cuttings. The methods and systems can evaluate one or more of the fluid parameters in conjunction with other fluid parameters typically accounted for in well hydraulics to determine a drilling fluid formulation that optimizes the drilling fluid for effective transport of drill cuttings. Methods and systems are also provided that evaluate one or more of the fluid parameters in conjunction with the other fluid parameters of a drilling fluid to determine operating parameters that optimize a drilling operation for effective transport of drill cuttings.

The four fluid parameters for a drilling fluid include: a first fluid parameter (e.g., Mason number or critical shear rate based on Mason number) for the drilling fluid and a particular drilling operation, wherein the first fluid parameter relates to the shear forces that break apart components (i.e., colloidal or polymer gel components) of the drilling fluid during the particular drilling operation; a second fluid parameter (e.g., dimensionless mixing number or mixing parameter) for the drilling fluid and the particular drilling operation, wherein the second fluid parameter characterizes mixing of drill cuttings with the drilling fluid during the particular drilling operation; and third and fourth fluid parameters (e.g., a first normal stress coefficient $\Psi_1$, an $N_1$ stress difference, or another suitable rheological parameter; a second normal coefficient $\Psi_2$ of the drilling fluid, an $N_2$ stress difference, or another suitable rheological parameter) for the drilling fluid and the particular drilling operation, wherein the third and fourth parameters characterizes normal stresses (excluding pressure) in the drilling fluid during the drilling operation; this normal stress has been shown to place drilling cuttings locally into the highest velocity zone of the axial flow.

FIGS. 1A and 1B illustrate a workflow that measures the four fluid parameters for a drilling fluid and evaluates these fluid parameters in conjunction with other fluid parameters to determine a drilling fluid formulation that optimizes the drilling fluid for effective transport of drill cuttings.

The workflow begins in block 1001 by obtaining one or more samples of a drilling fluid.

In block 1003, the workflow measures or calculates a first fluid parameter (e.g., Mason number or critical shear rate based on Mason number) for the drilling fluid sample(s) of 1001 and a particular drilling operation. The particular drilling operation can be characterized by a number of operating parameters, such as drill bit/hole size, drill pipe size, drilling fluid flow rate, rotational speed of the drill string, viscosity of the drilling fluid at the appropriate shear rate for the flow rate and rotational speed, cutting size and densities of the drilling fluid and the drilling cuttings (or differences therebetween). The operating parameters can vary across different drilling operations/jobs at the same wellsite or at different wellsites. The particular drilling operation can be planned for use in an individual well or formation and tailored for that specific application. Alternatively, the particular drilling operation can be generalized for use in a certain type of well or formation and tailored for the more generalized application.

For a drilling fluid incorporating a colloidal system (such as an oil-based mud), the Mason number of the drilling fluid characterises the balance between shear forces destroying the gel and adhesive forces building the gel as follows:

$$Mn = \frac{F_{shear}}{F_{adhesive}} = \frac{6\pi\eta_0(2r+\varepsilon)\dot{\gamma}}{V_0/\varepsilon}, \qquad \text{Eqn. (1)}$$

where Mn is the Mason number, r is the size of the dispersive phase component in the drilling fluid, $\varepsilon$ is the range of the interaction potential for the drilling fluid (typical estimate being $\varepsilon\sim0.1$ r for depletion envisaged in this function), no is the fluid viscosity of the continuous phase in the drilling fluid, y is the shear rate imposed on the drilling fluid, and $V_0$ is depth of the effective interaction potential.

Eqn. (1) can be restated using measurable and estimated parameters as follows:

$$Mn = \frac{12\pi\eta_0\phi^2 G_{10}}{\sigma_y^2}\left(\frac{\varepsilon}{r}\right)\dot{\gamma}, \qquad \text{Eqn. (2)}$$

where Mn is the Mason number, $\eta_0$ is the fluid viscosity of the continuous phase in the drilling fluid, $\phi$ is the volume fraction of the dispersed phase in the drilling fluid, $G_{10}$ is the short time elastic modulus (at 10 second sample age) of the drilling fluid, $\sigma_y$ is the dynamic yield stress of the drilling fluid, $\varepsilon$ is the range of the interaction potential for the drilling fluid, r is the size of the dispersed-phase component in the drilling fluid, and $\dot{\gamma}$ is the shear rate imposed on the drilling fluid.

The short time elastic modulus $G_{10}$ is not typically measured. However, the gel-strength S of the drilling fluid can be measured. Given that the drilling fluid (e.g., OBM gel) fails at a strain of approximately 10% means that the short time elastic modulus $G_{10}$ can be approximated as:

$$G_{10} \approx \frac{S}{\gamma_{break}} \approx \frac{S}{0.1}. \qquad \text{Eqn. (3)}$$

Note that the shear rate y within the drilling fluid arises through axial flow and rotation, and thus the shear rate y can be estimated from the operating parameters of the drilling operation as:

$$\dot{\gamma} = \frac{\sqrt{((u_o)^2 + (R_i\omega)^2}}{(R_o - R_i)}, \text{ and} \qquad \text{Eqn. (4a)}$$

$$u_0 = \frac{Q}{\pi(R_o^2 - R_i^2)}, \qquad \text{Eqn. (4b)}$$

where $R_o$ is the outer radius of the drill pipe, $R_i$ is the radius of the drilled borehole, $\omega$ is the angular velocity of the drill string/drill bit, and Q is the flow rate of the drilling fluid.

For the drilling fluid incorporating a colloidal system (such as an oil-based mud), the Mason number Mn can be characterized by analysis of hysteresis seen in a flow curve measurement performed by an automated rheometer (e.g., rheoprofiler). The flow curve measurements can be configured according to operating parameters of the particular drilling operation selected from the group consisting of: drill pipe radius, drilled borehole radius, angular velocity of the drill string/drill bit, and drilling fluid flow rate. The flow curve measurements can be performed from high shear rate ($1000$ s$^{-1}$) to low shear rate (e.g., $0.1$ s$^{-1}$) and then immediately increasing to $1000$ s$^{-1}$. Other protocols can be used, e.g., inserting a waiting period after the lowest shear rate, or logarithmically increasing the time per point as the measurement proceeds to low shear rate. The purpose is to see hysteresis, that is a different curve going from high to low compared to going from low to high. The critical shear rate is then the boundary between where the two curves being apart at lower shear rates, overlay at higher shear rates. If the flow curve hysteresis is measured, then Mn=1 occurs at the lowest shear rate (i.e., critical shear rate $\dot{\gamma}_c$) for which the measurement is history independent (so, in a downsweep followed by upsweep, where the curves come back together). The critical shear rate $\dot{\gamma}_c$ can be used as the first parameter (or part thereof).

For drilling fluid incorporating a polymer system (such as a water-based mud), the underlying structure of the drilling fluid is different, and an alternative approach is required. For such polymer systems, the gel breaks at a strain of ~100%. Hence, the shear-stress on the fluid side at the failure boundary around a particle can be equated to the elastic stress on the solid side of the failure boundary assuming a strain of 100%. Hence, $$Mn = \frac{K\dot{\gamma}}{G}, \qquad \text{Eqn. (5)}$$

where Mn is the Mason number, K is the plastic viscosity of the drilling fluid when fitted with a standard Bingham model, G is the short time elastic modulus (at 10 second sample age) of the drilling fluid, equal to the 10 s gel strength since the gel fails at a strain of approximately 100%, and $\dot{\gamma}$ is the shear rate imposed on the drilling fluid.

Here, the shear rate $\dot{\gamma}$ of the drilling fluid can be estimated from the operating parameters of the drilling operation as described above with respect to Eqns. (4a) and (4b).

Note that in all cases the drilling fluid promotes transport of cuttings when the Mason number Mn<1 and/or the critical shear rate $\dot{\gamma}_c$ of the drilling fluid is at least $50$ s$^{-1}$ (or possibly greater than $400$ s$^{-1}$, or possibly greater than $800$ s$^{-1}$).

In block 1005, the workflow measures or calculates the second fluid parameter (e.g., dimensionless mixing number or mixing parameter) for the drilling fluid sample(s) of 1001 and the particular drilling operation.

In embodiments, the second fluid parameter can represent a dimensionless mixing number ($\Xi$) based on the combination of a Froude number and a Shields number for the drilling fluid sample(s) of 1001. The Shields number characterizes the movement of particles (drilling cuttings) from a bed into fluid flow based on the balance between the viscous stresses pulling particles from the bed and the gravitational force keeping them in place as follows:

$$\theta = \frac{3\sigma}{2(\rho_s - \rho_f)ga}, \qquad \text{Eqn. (6)}$$

where $\theta$ is the Shields number, $\sigma$ is the viscous stress acting on the particles (drill cuttings), $\rho_s$ is the characteristic density of the particles (drilling cuttings), $\rho_f$ is the fluid density of the drilling fluid, g is the gravitational constant, and a is the characteristic radius of the particles (drill cuttings).

The dimensionless mixing number ($\Xi$) can be derived from the Shields number of Eqn. (6) and operating parameters of the drilling operation as:

$$\Xi = \left(\frac{Ta}{n} + 1\right)\theta = \left(\frac{\rho_f \omega R_i H}{n\eta}\sqrt{\frac{H}{R_i}} + 1\right)\frac{3}{2(\rho_s - \rho_f)ga}\eta\frac{R_i\omega}{H}, \qquad \text{Eqn. (7)}$$

where $\Xi$ is the dimensionless number based on the combination of a Froude number and a Shields number for the drilling fluid, Ta is the Taylor number which is the ratio of inertial to viscous stresses (note Froude number is Fr=Ta. $\theta$), $\rho_s$ is the characteristic density of the particles (drill cuttings), $\rho_f$ is the fluid density of the drilling fluid, a is the characteristic radius of the particles (drill cuttings), $R_i$ is the radius of the drilled borehole, $\omega$ is the angular velocity of the drill string/drill bit, n is the viscosity of the drilling fluid at the appropriate shear rate, H is the gap between the drill pipe and the borehole (H=Ri−Ro), g is the gravitational constant, and n is an experimentally determined scale factor, (e.g., n=125).

In embodiments, the dimensionless number $\Xi$ can be used to collapse disparate mixing measurements from x-ray adsorption experiments performed on a sample of the drilling fluid in a rotating horizontal Couette device as illustrated in FIG. 2A. In this embodiment, a mixing parameter $\Lambda$ can be measured by intensities values that result from the x-ray adsorption experiments. Specifically, because x-ray adsorption at low concentration is expected to follow Beer's law, the measured intensity (1) can be related to the incident intensity ($I_o$) as follows:

$$\ln(I) = \ln(I_o) - k_w x_{w1} - k_f x_f - k_p x_p - k_w x_{w2}, \qquad \text{Eqn. (8)}$$

where I is the measured intensity, $I_o$ is the incident intensity, $k_w$, $k_f$, $k_p$ are extinction coefficients for the wall material, the fluid and the particles, respectively, and $x_{w1}$, $x_f$, $x_p$, $x_{w2}$ is the path length of the first wall, the fluid, the particles and the second wall respectively for a particular ray.

Given the particle volume fraction $\phi$, then $x_f = (1-\phi)x_{comp}$ and $x_p = \phi x_{comp}$, where x comp is the path length across a Couette device filled with a composition of particles and fluid as shown schematically in FIG. 2B. If we consider the image in comparison with an image of the fluid filled Couette device without particles, $I_{empty}$, then for each pixel, $$\ln(I) - \ln(I_{empty}) = -\phi(k_p - k_f)x_{comp}. \qquad \text{Eqn. (9)}$$

The mixing parameter $\Lambda$ can be related to intensities measured during the x-ray adsorption experiments as follows:

$$\Lambda = \frac{2\phi_{top}}{\phi_{top} + \phi_{bottom}} = \frac{2[\ln(I) - \ln(I_{empty})]_{top}}{[\ln(I) - \ln(I_{empty})]_{top} + [\ln(I) - \ln(I_{empty})]_{bottom}}, \qquad \text{Eqn. (10)}$$

where $\Lambda$ is the mixing parameter for the drilling fluid, and the suffixes top and bottom denote symmetrically disposed image regions at the top and bottom of the Couette device.

At zero or low rotation rates, the particles sediment to form a bank at the bottom of the Couette device and $\Lambda=0$, albeit with some movement leading to redistribution. At higher rotation rates, the drag caused by the flow is sufficient to overcome gravity and the particles are carried around the Couette device. At sufficiently high rotation rates, the particles are expected to be fully mixed in the drilling fluid so that there would be an equal volume fraction of particles at the top and bottom of the Couette device so that $\Lambda=1$. The mixing parameter $\Lambda$ can be plotted as a function of rotation rate w of the Couette device. Until a critical rotation rate, the particles remain at the bottom of the Couette device so that $\Lambda=0$. Above the critical rotation, the mixing increases monotonically until at very high rotation rates the parameter appears to saturate. The critical rotation rate is not dependent on the initial volume of particles and appears to be only weakly dependent on viscosity.

Figure 2C:
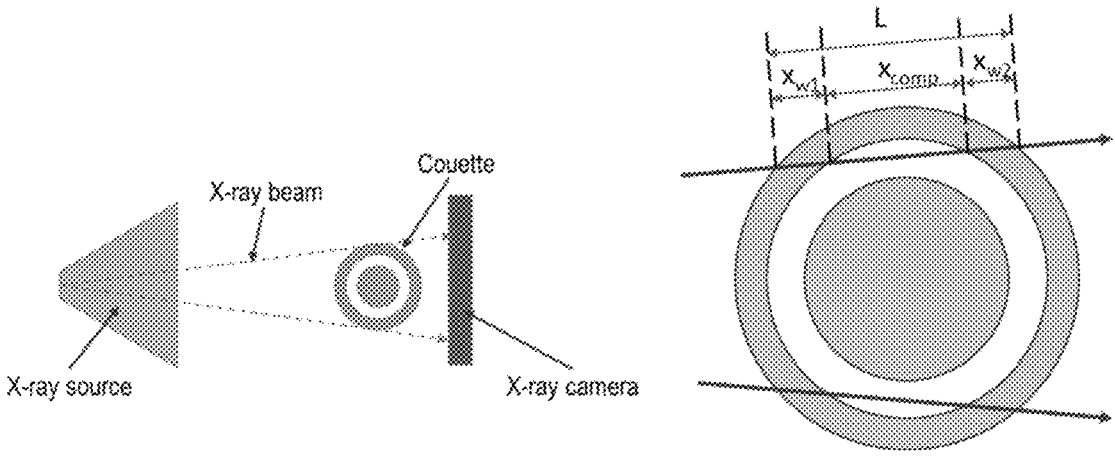
FIG. 2C is a plot of a mixing parameter ($\Lambda$) of a drilling fluid as function of dimensionless mixing number ($\Xi$)
Figure 2C:
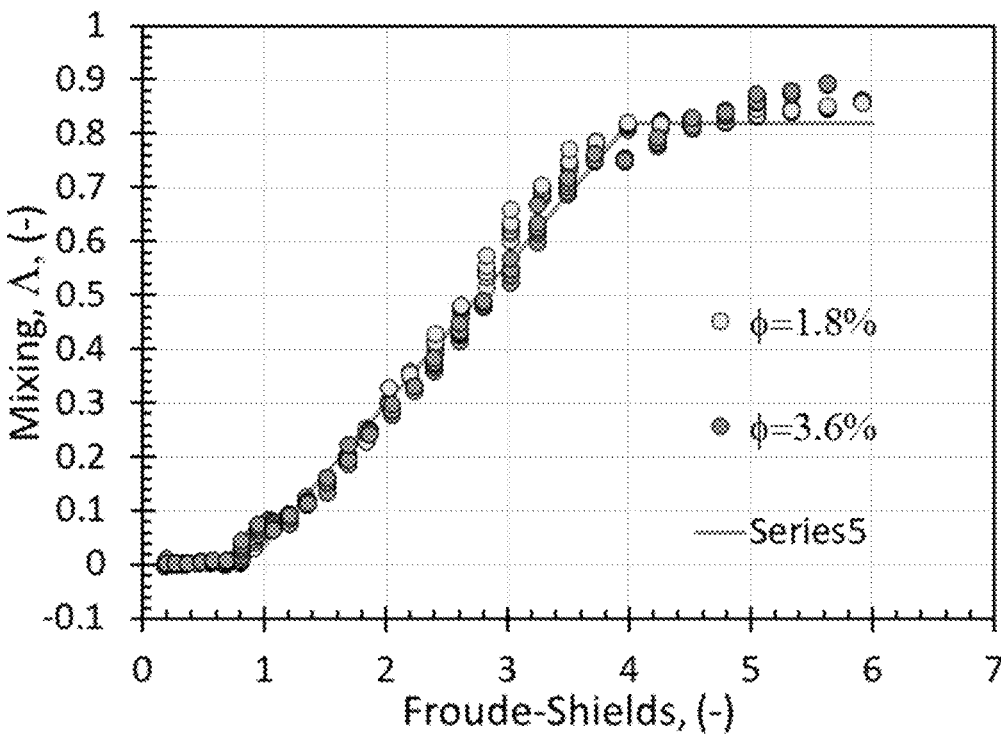

The mixing parameter $\Lambda$ is a function of the drilling process and drilling fluid parameters. The important process and fluid parameters may be combined as a single dimensionless mixing number $\Xi$, so that $\Lambda=f(\Xi)$ with f( ) being a single monotonic function as shown in FIG. 2C, which can be represented by a piecewise mathematical expression of the form:

$$\Lambda_M = \begin{cases} 0, & \Xi < 0.85 \\ 0.26\Xi - 0.221, & 0.85 \le \Xi \le 4 \\ 0.82, & \Xi > 4 \end{cases} \qquad \text{Eqn. (11)}$$

Hence, the dimensional number E represents the mixture of forces that are responsible for particle mixing, and $\Lambda$ is a number characterising the actual mixing. Note that in all cases the drilling fluid promotes transport of cuttings when the dimensionless mixing number E is at least 1 (or possibly greater than 3). For the dimensionless mixing number above about 4, the cuttings are fully mixed and hence further increasing, for example, further drill-string rotation will not improve mixing, but may damage the drill-string. Additionally or alternatively, the mixing parameter $\Lambda$ can be evaluated to characterize the transport of cuttings in the drilling fluid.

In block 1007, the workflow measures or calculates the third and fourth fluid parameters for the drilling fluid sample(s) of 1001 and the particular drilling operation. In embodiments, the third fluid parameter can represent a first normal stress coefficient $\Psi_1$, an $N_1$ stress difference, or another suitable rheological parameter of the drilling fluid; and the fourth fluid parameter can represent a second normal coefficient $\Psi_2$ of the drilling fluid, an $N_2$ stress difference, or another suitable rheological parameter of the drilling fluid.

The $N_1$ stress difference and the $N_2$ stress difference can be measured using standard methodology as described in R. J. Poole, "Measuring normal-stresses in torsional rheometers: a practical guide", BSR Bulletin, 57 (2016), and Maklad, R. J. Poole, "A review of the second normal-stress difference; its importance in various flows, measurement techniques, results for various complex fluids and theoretical predictions", Journal of Non-Newtonian Fluid Mechanics, 292 (2021). The shear rate y can be estimated. For example, a typical average shear rate in a well with rotation can be estimated as $\dot{\gamma}=100$ s$^{-1}$. In many cases, the drilling fluid promotes transport of cuttings when the first normal stress coefficient $\Psi_1$ is greater than 2 mPa·s$^{-2}$. For polymer systems, the drilling fluid promotes transport of cuttings when $\Psi_1 > -\Psi_2$ (see O. Maklad and R. J. Poole, "A review of the second normal-stress difference; its importance in various flows, measurement techniques, results for various complex fluids and theoretical predictions", Journal of Non-Newtonian Fluid Mechanics, 2021, Volume 292, 104522). For drilling fluid clay based colloidal systems, the drilling fluid promotes transport of cuttings when $\Psi_2 > 0$ and $\Psi_1 \approx 0$.

Steady state simple shear may be considered as the most common flow type investigated in rheology and so is known as the standard/classic flow for rheological measurements. In a simple shear flow, the flow field is known to have a rectilinear distribution with layers of fluid sliding past each other. To understand the behavior of different fluids, it is traditional to study the response of stress tensor in such flow conditions. The stress response may be presented as in a tensorial form as:

$$\tau = \begin{pmatrix} \tau_{xx} & \tau_{xy} & \tau_{xz} \\ \tau_{yx} & \tau_{yy} & \tau_{yz} \\ \tau_{zx} & \tau_{zy} & \tau_{zz} \end{pmatrix}. \qquad \text{Eqn. (12)}$$

For Newtonian fluids the shear components of the stress tensor $\tau_{xy}$ in simple shear flow conditions finds a non-zero value and is characterized by a material property known as the viscosity of fluid. The other shear components are zero in simple shear (The $\tau_{xz} = \tau_{yz} = 0$). For Newtonian fluids the diagonal components are also zero (when pressure is subtracted), i.e., normal stresses $\tau_{xx} = \tau_{yy} = \tau_{zz} = 0$. On the contrary, for non-Newtonian fluids, these diagonal components might find non-zero values. This arises because of the presence of microstructure within the fluid. The sign and magnitude of the diagonal stress components then depend on different parameters such as the shape and flexibility of such microstructures under the particular flow condition.

For an incompressible fluid it is not possible to measure all the extra stresses in the normal directions because the pressure is an undefined dynamical variable. In rheometry, the pressure is determined by evaluating a total normal stress $\sigma_{ii}$ at a boundary; in a cone-plate geometry, simplifying to cartesian coordinates for clarity, for example, $\sigma_{xx} = -p + \tau_{xx} = 0$ at the free surface (with the assumption that the free surface is an arc of a circle), so $p = \tau_{xx}$ and $\sigma_{yy} = -p + \tau_{yy} = -\tau_{xx} + \tau_{yy} = -N_1$, which is why the total force on the upper plate is equal to the coefficient of first normal stress difference $N_1$ multiplied by area of the upper plate. Using a similar analysis, in a parallel plate geometry the normal force acting on the plate is a function of first and second normal stress differences $N_1$, $N_2$. In one example, FIG. 2F illustrates a combination of a cone and plate measurement and a parallel plate measurement that can be used to determine the first and second normal stress differences $N_1$, $N_2$.

In a general flow there are three normal stresses $\tau_{xx}$, $\tau_{yy}$ and $\tau_{zz}$. The first and second normal stress differences are defined as:

$$N_1(\dot{\gamma}) = \tau_{xx} - \tau_{yy} = \Psi_1(\dot{\gamma})\dot{\gamma}^2 \qquad \text{Eqn. (13)}$$

$$N_2(\dot{\gamma}) = \tau_{yy} - \tau_{zz} = \Psi_2(\dot{\gamma})\dot{\gamma}^2$$

Hence, the first and second normal stress differences $N_1$, $N_2$ do not depend on the (arbitrary) absolute pressure. The first normal stress differences $N_1$ is a function of the first normal stress coefficient $\Psi_1$ and shear rate. The second normal stress difference $N_2$ is a function of the second normal stress coefficient $\Psi_2$ and shear rate. The first and second normal stress coefficients $\Psi_1$, $\Psi_2$ are material properties.

Other rheological parameters are related to the normal stress coefficients ($\Psi_1$ and $\Psi_2$), such as relaxation times, retardation time, mobility factor or other material properties derived from fitting constitutive models to complex rheological properties may be used. It will be understood by a person skilled in the art that such substitutions are materially equivalent. Using these other parameters as proxy for the normal stress coefficients will be understood to be included in this specification. It is interesting to note that it is common to only measure shear stress (the shear stress is characterized by a shear viscosity modulus). Normal stress difference measurements are neglected in most industries in general and the oil and gas industry in particular.

Detailed theoretical studies supported by experiment have suggested the first and second normal stress differences $N_1$, $N_2$ play important roles during the hole cleaning process while drilling. In particular, in drilling fluid with positive $N_1$, the flow become complex at lower rotation speeds due to the presence of Taylor vortices which is now known to be a key element during the hole cleaning process. Therefore, drilling fluids with positive $N_1$ are advantageous for hole cleaning process. In addition, in drilling fluids with negative value of $N_2$, the particles move from the area near walls to an area equidistant from the surrounding walls. In this location any transport due to axial flow velocity is maximized and hence the cuttings placed there will be carried further thereby improving hole cleaning. Further, the results indicate that, although having materials with negative $N_2$ will be beneficial for cuttings transport, very high values of $N_2$ could potentially reduce the complexity of flow field (and so will counteract the effect of $N_1$). The results show that for drilling fluids with positive $N_1$ and negative $N_2$, the best efficiency of transport of cuttings is provided when $$0.05 < -\frac{N_2}{N_1} < 1,$$

preferably $$0.2 < -\frac{N_2}{N_1} < 0.5.$$

Note that $-N_2/N_1 = -\Psi_1\Psi_2$.

In block 1009, the workflow measures or calculates one or more additional fluid parameters of the drilling fluid sample(s) of 1001 and the particular drilling operation. The additional fluid parameters can be fluid parameters typically accounted for in well hydraulics and measured by well-known techniques as part of mud logging operations. For example, such additional fluid parameter(s) can include the R6 rheological parameter, ECD, other conventional parameters listed in API 13B-2, "Recommended practice for Field Testing Nonaqueous-based Drilling Fluids", Sixth Edition, 2023, or other suitable fluid parameters such as time to gelation (time after cessation of shear after which G'>G"), linear viscoelastic moduli, non-linear viscoelastic moduli, characteristic time (inverse of frequency for which G'=G", or in the presence of background shear (parallel superposition) for which G'∥=G"∥ (see E. Tran and A. Clarke, "The relaxation time of entangled HPAM solutions in flow", Journal of Non-Newtonian Fluid Mechanics, 2023, Volume 311, 104954.), yield strain, stress relaxation modulus, LAOS (Bowditch curves analysis), MAOS measurement of SPP traces (see e.g., A. Clarke, "Gel breakdown in a formulated product via accumulated strain", Soft Matter, 2021, 17, 7893-7902), slip onset shear rate.

In block 1011, at least one of the first fluid parameter, the second fluid parameter, the third fluid parameter, and the additional fluid parameter(s) can be evaluated, for example, in conjunction with predefined criteria that predicts that the drilling fluid will provide effective transport of drill cuttings.

For example, the predefined criteria can be configured to check that the critical shear rate $\dot{\gamma}_c$ of the drilling fluid is at least 50 s$^{-1}$. In another example, the predefined criteria can be configured to check that the critical shear rate $\dot{\gamma}_c$ of the drilling fluid is greater than 400 s$^{-1}$. In yet another example, the predefined criteria can be configured to check that the critical shear rate c of the drilling fluid is greater than 800 s$^{-1}$. In still another example, the predefined criteria can be configured to check that the Mason number at the shear rate of interest of the drilling fluid is less than 1.

In another example, the predefined criteria can be configured to check that the dimensionless mixing number ($\Xi$) of the drilling fluid and the particular drilling operations is greater than 1. In yet another example, the predefined criteria can be configured to check that the dimensionless mixing number ($\Xi$) of the drilling fluid and the particular drilling operations is greater than 3.

In another example, the predefined criteria can be configured to check that the first normal stress coefficient $\Psi_1$ is greater than 2 mPa·s$^{-2}$. In another example, for polymer systems, the predefined criteria can be configured to check that $\Psi_1 > -\Psi_2$. In yet another example, for drilling fluid clay based colloidal systems, the predefined criteria can be configured to check that $\Psi_2 > 0$ and $\Psi_1 \approx 0$.

In yet another example, the predefined criteria can be configured to check that the first normal stress difference $N_1$ is positive (i.e., $N_1 > 0$). Additionally or alternatively, the predefined criteria can be configured to check that, for the case where the first normal stress difference $N_1$ is positive and the second normal stress difference $N_2$ is negative, the ratio $-N_2/N_1$ (or the corresponding ratio $-\Psi_2/\Psi_1$) is within the range between 0.5 and 1, and/or the ratio $-N_2/N_1$ (or the corresponding ratio $-\Psi_2/\Psi_1$) is within the range between 0.2 and 0.5.

In block 1013, the formulation of the drilling fluid can be modified (for example by adding one or more polymer additives or other components) based on the evaluation of 1011. Furthermore, the operations of 1001 to 1013 can be repeated for one or more iterations with modified drilling fluid to determine a drilling fluid formulation that optimizes the drilling fluid for effective transport of drill cuttings. In embodiments, the drilling fluid formulation that optimizes the drilling fluid for effective transport of drill cuttings can enable higher ROP of the drill bit during the drilling operation by maximizing cuttings transport in the drilling fluid during the drilling operation.

In block 1015, the drilling fluid formulation determined in 1013 can be used in the particular drilling operation.

In other embodiments, the evaluation of block 1011 can be based on one or more parameters derived from the first fluid parameter (e.g., Mason number) and/or the second fluid parameter (e.g., dimensionless mixing number) of the drilling fluid and the particular drilling operation. For example, the evaluation of block 1011 can be based on a transport efficiency metric τ derived as a function of a settling factor L* and the dimensionless mixing number of the drilling fluid.

Figure 2D:
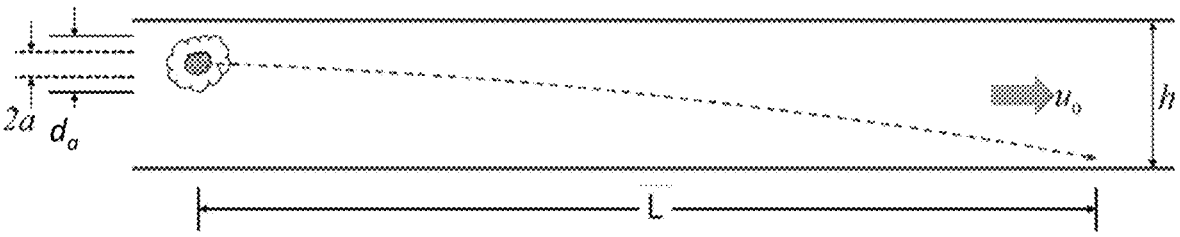
FIG. 2D is a schematic diagram of a model of simple Stokes settling that can be used to derive a settling factor for a drilling fluid in accordance with the present disclosure.

In embodiments, the settling factor L* can be derived from a model of simple Stokes settling shown in FIG. 2D, where the time for a particle to sediment multiplied by the axial velocity will give the distance, L, over which a particle travels before reaching the bottom of the channel. If it is assumed that there is no (axial) slip between the particle and the flowing fluid, then $L=u_0\Delta t$. With $\Delta t$ being the time for the particle to settle a characteristic distance h, the dimensionless settling factor L* can be defined as:

$$L^* = \frac{L}{h} = u_0 \frac{9\eta(\dot{\gamma})d_a(M_n)}{2a^3(\rho_s - \rho_f)g},$$ Eqn. (14a)

$d_a=2(a+\delta)$, which can be approximated from the Mason number as $$d_a(Mn) = \begin{cases} \frac{2a}{Mn}, & Mn < 1 \\ 2a, & Mn \geq 1 \end{cases}$$ Eqn. (14b)

where $u_0$ is derived from operating parameters of the drilling operation according to Eqn. (4b) above, $\dot{\gamma}$ is derived from operating parameters of the drilling operation according to Eqn. (4a) above, $M_n$ is the Mason number for the drilling fluid and the drilling operation as calculated or measured above, a is the characteristic radius of the drilling cuttings, δ is an accreted gel thickness. $\rho_s$ is the density of the drill cuttings, $\rho_f$ is the fluid density of the drilling fluid, and g is the gravitational constant.

Note that the parameter $d_a$ is based on the cutting size a together with an accreted gel thickness δ. In this manner, the accreted gel thickness δ will hinder settling by causing greater drag due to size. Hence, the more accreted gel the further the carriage of the particle before it can settle.

Figure 2E:
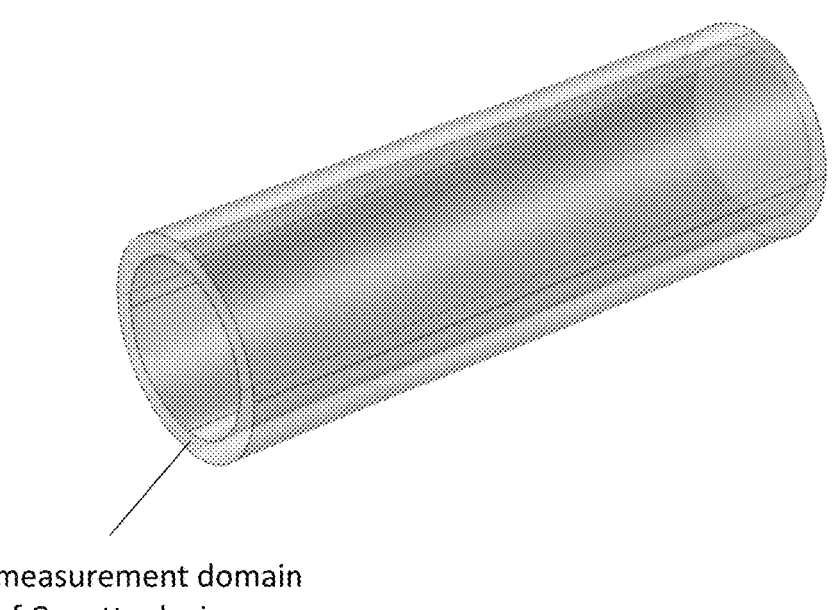
FIG. 2E is a schematic diagram of a concentric Couette device that can be used to derive a transport efficiency metric for a drilling fluid, where the transport efficiency metric is a function of a settling factor and the mixing number of the drilling fluid in accordance with the present disclosure.
Figure 2F:
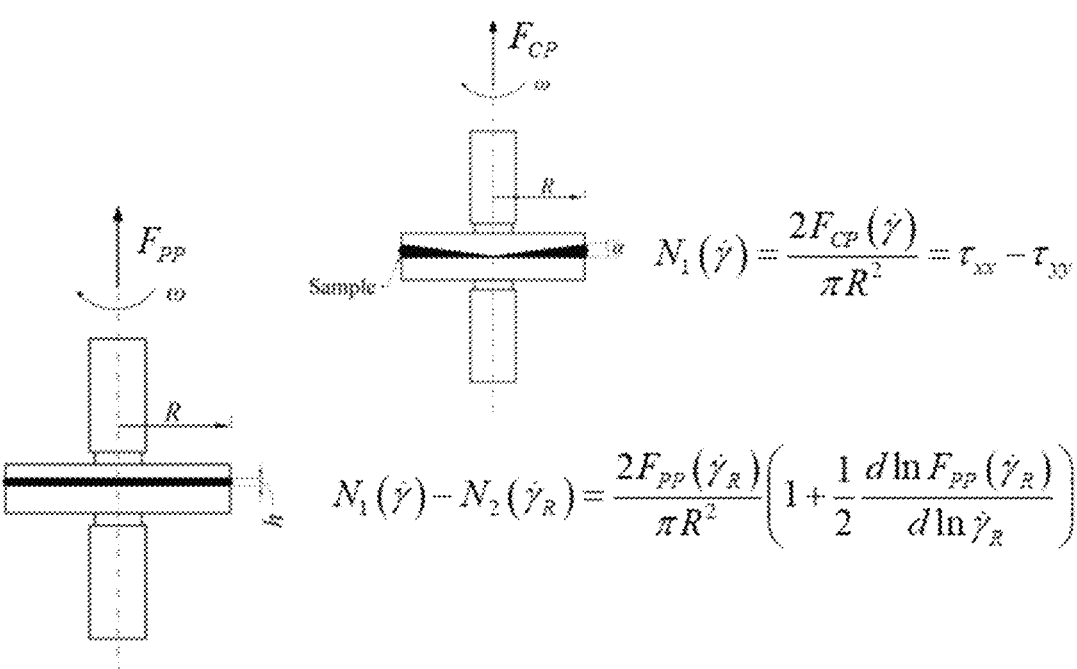
FIG. 2F is a schematic diagram that illustrates a combination of a cone and plate measurement and a parallel plate measurement that can be used to determine first and second normal stress differences of a drilling fluid.

To derive a transport efficiency metric τ as a function of the settling factor L* and the dimensionless mixing number of the drilling fluid, experiments can be performed in a concentric Couette device with the axial length much larger (e.g., thirty times) than the Couette gap. To extend the axial length of the Couette device to cover that expected length L of settling is impractical. Thus, the experiments can be configured to measure the time taken to clear a fraction f (e.g., 90%) of particles from the measurement domain of the Couette device as shown in FIG. 2E. A steady state distribution of particles is loaded into the measurement domain based on periodic boundary conditions. The experiment then continues to turn off the supply of particles to the inlet and dispose of particles at the outlet, so that the total number of particles in the measurement domain falls, while calculating the elapsed time when the number of particles remaining in the measurement domain is 1-f. That elapsed time is stored as the transport efficiency metric τ (L*,Ξ). The experiment can be performed for several values of L*, Ξ, so that a surface t (L*,Ξ) can be interpolated that defines the transport efficiency metric τ as a function of a settling factor L* and the dimensionless mixing number of the drilling fluid.

In another embodiment, a transport efficiency metric can be derived by integrating cuttings flux over the outlet area of the Couette device as follows:

$$\Phi_{TE} = \frac{\int u_z^p \phi dS}{A * ROP}.$$ Eqn. (15)

In this case, the numerator represents the integral of local particle flux across the outlet area and the denominator is the rate of cuttings generation. Thus, $\Phi_{TE}=1$ when all cuttings are convected, and $\Phi_{TE}<1$ if cuttings are accumulated. If $\Phi_{TE}>1$, then the calculation indicates that cuttings can be convected more rapidly than they are being generated so that accumulated cuttings beds may be cleaned.

In yet another embodiment, a transport efficiency metric can be derived by integrating cuttings flux over the outlet area of the Couette device as follows:

$$\Phi_{FLUX} = \frac{\int u_z^p \phi dS}{\frac{Q}{V}\int \phi dV}.$$ Eqn. (16)

In this case, the numerator represents the integral of local particle flux across the outlet area and the denominator is the integral of particle flux convected with the fluid flow. Thus, $\Phi_{FLUX}<1$ is a figure of merit with the larger value being closer to best possible cleaning but the difference from 1 indicating the amount of stationary bed of cuttings.

Figure 3A:
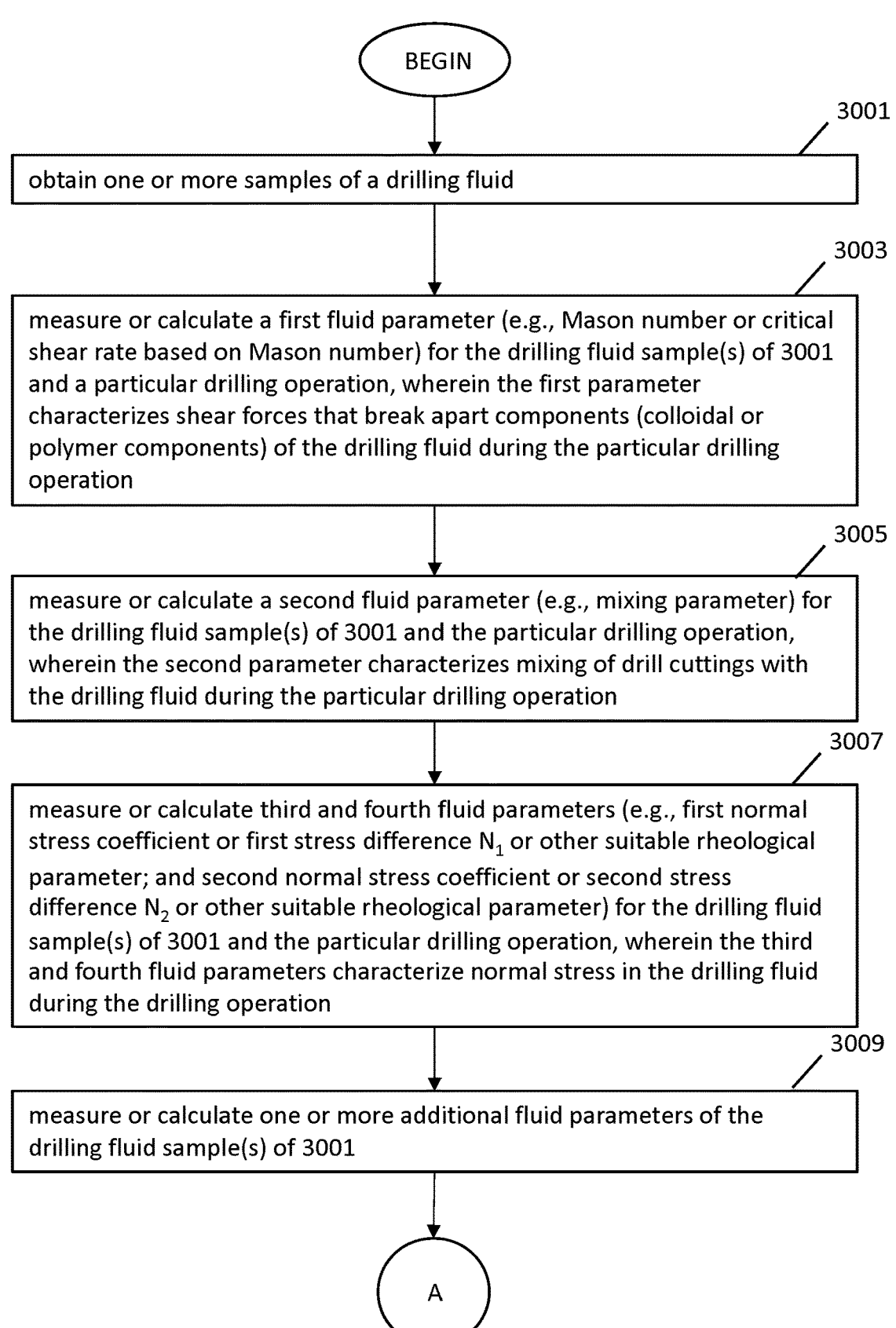
FIGS. 3A and 3B, collectively, is a flowchart of a workflow that measures four fluid parameters for a drilling fluid and evaluates these fluid parameters in conjunction with other fluid parameters to determine operational parameters for the drilling operation used in conjunction with drilling fluid that optimizes the operational parameters for effective transport of drill cuttings.
Figure 3B:
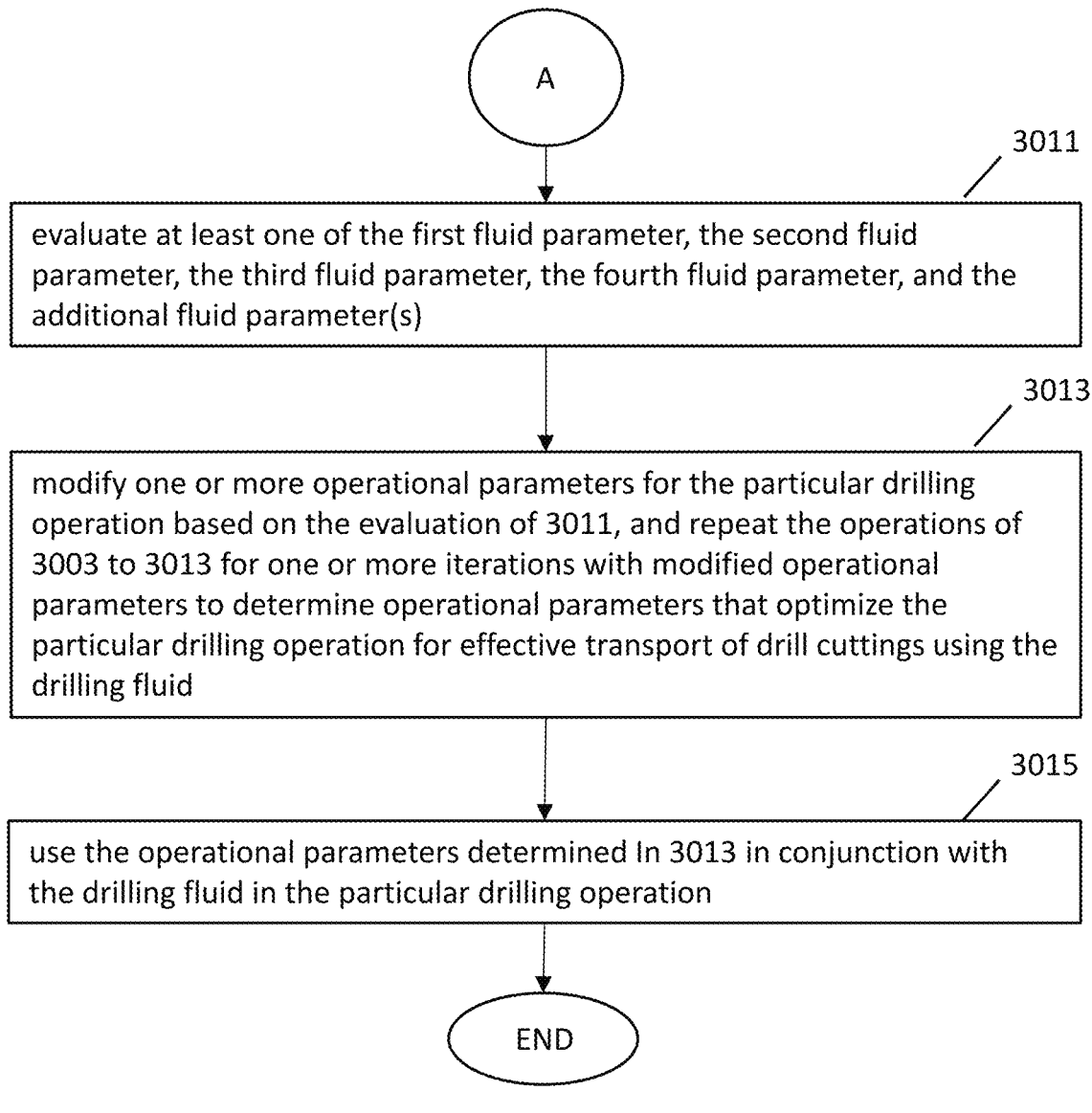

FIGS. 3A and 3B illustrate a workflow that measures the four fluid parameters for a drilling fluid and evaluates these fluid parameters in conjunction with other fluid parameters to determine operational parameters for the drilling operation used in conjunction with drilling fluid that optimizes the operational parameters for effective transport of drill cuttings.

The workflow begins in block 3001 by obtaining one or more samples of a drilling fluid.

In block 3003, the workflow measures or calculates a first fluid parameter (e.g., Mason number or critical shear rate based on Mason number) for the drilling fluid sample(s) of 3001 and a particular drilling operation. The particular drilling operation can be characterized by a number of operating parameters, such as drill bit/hole size, drill pipe size, drilling fluid flow rate, rotational speed of the drill string, viscosity of the drilling fluid at the appropriate shear rate for the flow rate and rotational speed, cutting size and densities of the drilling fluid and the drilling cuttings (or differences therebetween). The operating parameters can vary across different drilling operations/jobs at the same wellsite or at different wellsites. The operations of 3003 can follow the operations of block 1003 as described above. The particular drilling operation can be planned for use in an individual well or formation and tailored for that specific application. Alternatively, the particular drilling operation can be generalized for use in a certain type of well or formation and tailored for the more generalized application.

In block 3005, the workflow measures or calculates the second fluid parameter (e.g., mixing number) for the drilling fluid sample(s) of 3001 and the particular drilling operation. The operations of 3005 can follow the operations of block 1005 as described above.

In block 3007, the workflow measures or calculates the third and fourth fluid parameters for the drilling fluid sample(s) of 3001 and the particular drilling operation. The third fluid parameter can represent a first normal stress coefficient $\Psi_1$, an $N_1$ stress difference, or another suitable rheological parameter of the drilling fluid. The fourth fluid parameter can represent a second normal coefficient $\Psi_2$ of the drilling fluid, an $N_2$ stress difference, or another suitable rheological parameter of the drilling fluid. The operations of 3007 can follow the operations of block 1007 as described above.

In block 3009, the workflow measures or calculates one or more additional fluid parameters of the drilling fluid sample(s) of 3001 and the particular drilling operation. The operations of 3009 can follow the operations of block 1009 as described above.

In block 3011, at least one of the first fluid parameter, the second fluid parameter, the third fluid parameter, the fourth fluid parameter, and the additional fluid parameter(s) can be evaluated, for example, in conjunction with predefined criteria that predicts that the drilling fluid will provide effective transport of drill cuttings. The operations of 3011 can follow the operations of block 1011 as described above. In other embodiments, the evaluation of block 3011 can be based on one or more parameters derived from the first fluid parameter (e.g., Mason number) and/or the second fluid parameter (e.g., dimensionless mixing number) of the drilling fluid and the particular drilling operation. For example, the evaluation of block 3011 can be based on a transport efficiency metric derived as a function of a settling factor L* and the dimensionless mixing number of the drilling fluid as described above.

In block 3013, one or more operational parameters of the drilling operation (such as drill bit/hole size, drill pipe size, drilling fluid flow rate, and/or rotational speed of the drill string) can be modified based on the evaluation of 3011. Furthermore, the operations of 3001 to 3013 can be repeated for one or more iterations with modified operational parameters to determine operational parameters that optimize the particular drilling operation for effective transport of drill cuttings using the drilling fluid. In embodiments, the operational parameters that optimize the particular drilling operation can enable higher ROP of the drill bit during the drilling operation by maximizing cuttings transport in the drilling fluid during the drilling operation.

In block 3015, the operational parameters of the drilling operation as determined in 3013 can be used in conjunction with the drilling fluid in the particular drilling operation.

In other embodiments, the evaluation of block 3011 can be based on one or more parameters derived from the first fluid parameter (e.g., Mason number) and/or the second fluid parameter (e.g., dimensionless mixing number) of the drilling fluid and the particular drilling operation. For example, a transport efficiency metric can be derived as a function of a settling factor L' and the dimensionless mixing number of the drilling fluid as described above.

Figure 4:
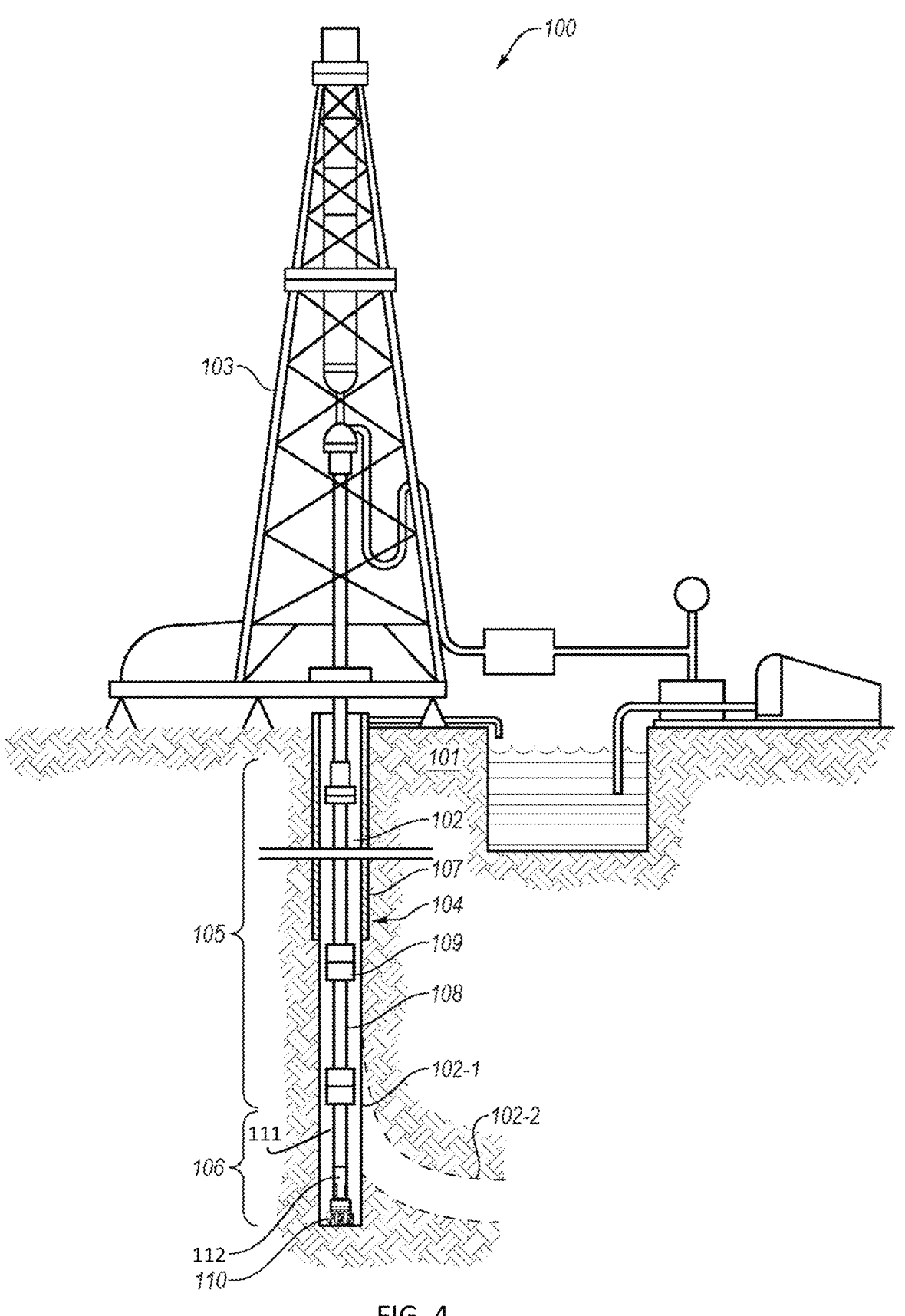
FIG. 4 is a schematic diagram of an example drilling system according to at least one embodiment of the present disclosure.

FIG. 4 illustrates an example drilling assembly 100 in which a drilling fluid as disclosed herein may be used. It should be noted that while FIG. 4 generally depicts a land-based drilling assembly, those skilled in the art will readily recognize that the principles described herein are equally applicable to subsea drilling operations that employ floating or sea-based platforms and rigs, without departing from the scope of the disclosure.

By way of example, FIG. 4 shows a drilling system 100 for drilling an earth formation 101 to form a wellbore 102. The drilling system 100 includes a drill rig 103 used to turn a drilling tool assembly 104 which extends downward into the wellbore 102. The drilling tool assembly 104 may include a drill string 105 operably coupled to a bottomhole assembly (BHA) 106 with a bit 110.

The drill string 105 can include several sections of drill pipe 108 connected end-to-end through tool joints 109. The drill string 105 transmits drilling fluid through a central bore and transmits rotational power from the drill rig 103 to the BHA 106 and the bit 110. In some embodiments, the drill string 105 may further include additional components such as subs, pup joints, etc. The drill pipe 108 provides a hydraulic passage through which drilling fluid is pumped from the surface. The drilling fluid discharges through nozzles, jets, or other orifices in the bit 110 for the purposes of cooling the bit 110 and cutting structures thereon, for lifting cuttings out of the wellbore 102 as it is being drilled, for controlling influx of fluids in the well, for maintaining the wellbore integrity, and for other purposes.

An example BHA 106 may include additional or other components (e.g., coupled between/to the drill string 105 and the bit 110). Examples of additional BHA components include a drill collar 111, stabilizers, measurement-while-drilling (MWD) tools, logging-while-drilling (LWD) tools, downhole motors, underreamers, section mills, hydraulic disconnects, jars, vibration or damping tools, other components, or combinations of the foregoing. The BHA 106 may further include a directional tool 112 such as a bent housing motor or a rotary steerable system (RSS). The directional tool 112 may include directional drilling tools that change direction of the bit 110, and thereby the trajectory of the wellbore. In some cases, at least a portion of the directional tool 112 may maintain a geostationary position relative to an absolute reference frame, such as gravity, magnetic north, or true north. Using measurements obtained with the geostationary position, the directional tool 112 may locate the bit 110, change the course of the bit 110, and direct the directional tool 112 on a projected trajectory. For instance, although the BHA 106 is shown as drilling a vertical portion 102-1 of the wellbore 102, the BHA 106 (including the directional tool 112) may instead drill directional or deviated well portions, such as directional portion 102-2.

In general, the drilling system 100 may include additional or other drilling components and accessories, such as special valves (e.g., kelly cocks, blowout preventers, and safety valves). Additional components included in the drilling system 100 may be considered a part of the drilling tool assembly 104, the drill string 105, or a part of the BHA 106 depending on their locations in the drilling system 100.

In some embodiments, the BHA 106 may include a downhole motor to power downhole systems and/or provide rotational energy for downhole components (e.g., rotate the bit 110, drive the directional tool 112, etc.). The downhole motor may be any type of downhole motor, including a positive displacement pump (such as a progressive cavity motor) or a turbine. In some embodiments, a downhole motor may be powered by the drilling fluid flowing through the drill pipe 108. In other words, the drilling fluid pumped downhole from the surface may provide the energy to rotate a rotor in the downhole motor. The downhole motor may operate with an optimal pressure differential or pressure differential range. The optimal pressure differential may be the pressure differential at which the downhole motor may not stall, burn out, overspin, or otherwise be damaged. In some cases, the downhole motor may rotate the bit 110 such that the drill string 105 may not be rotated at the surface, or may rotate at a different rate (e.g., slower) than the rotation of the bit 110.

The bit 110 in the BHA 106 may be any type of bit suitable for degrading downhole materials such as earth formation 101. Example types of drill bits used for drilling earth formations are fixed-cutter or drag bits, roller cone bits, and combinations thereof. In other embodiments, the bit 110 may be a mill used for removing metal, composite, elastomer, other downhole materials, or combinations thereof. For instance, the bit 110 may be used with a whipstock to mill into casing 107 lining the wellbore 102. The bit 110 may also be a junk mill used to mill away tools, plugs, cement, other materials within the wellbore 102, or combinations thereof. Swarf or other cuttings formed by use of a mill may be lifted to surface or may be allowed to fall downhole. In still other embodiments, the bit 110 may include a reamer. For instance, an underreamer may be used in connection with a drill bit and the drill bit may bore into the formation while the underreamer enlarges the size of the bore.

Figure 5:
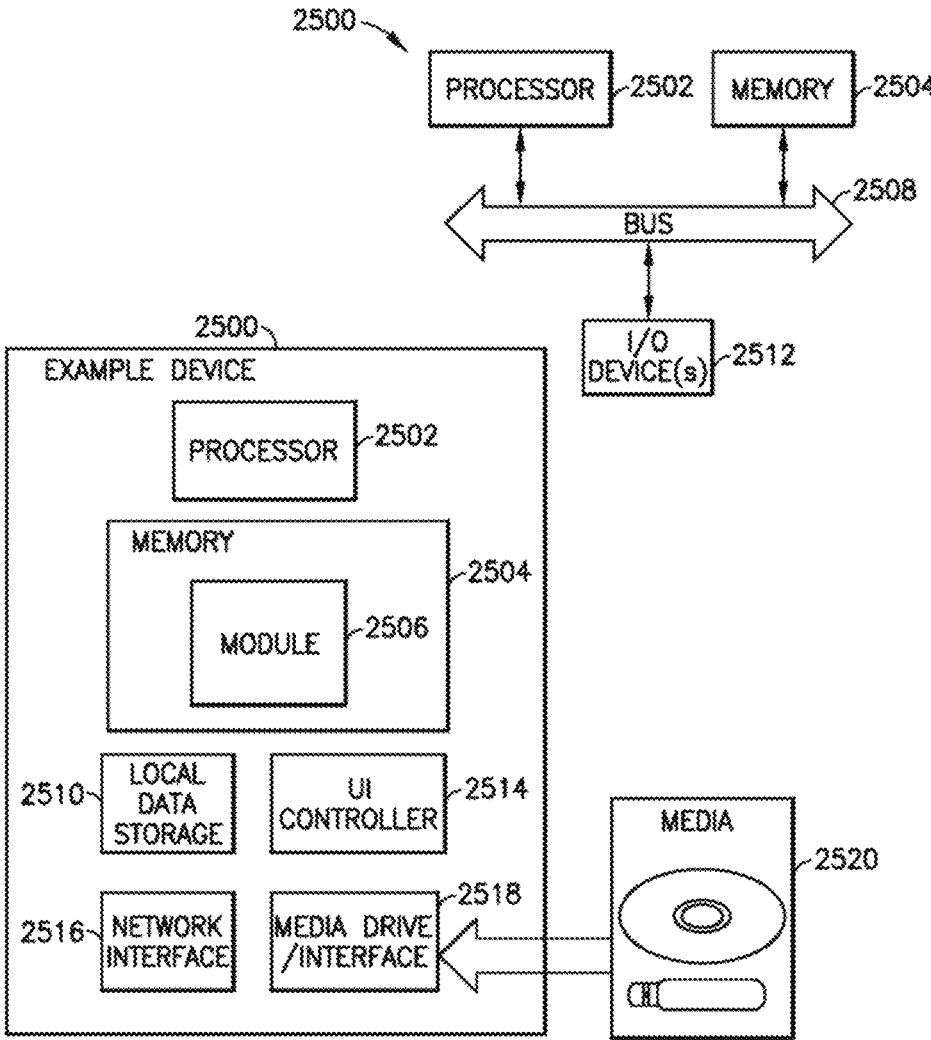
FIG. 5 is a block diagram of a computer processing system.

FIG. 5 illustrates an example device 2500, with a processor 2502 and memory 2504 that can be configured to implement various embodiments of the processes and systems as discussed in the present application. For example, various steps or operations of the processes or systems as described herein can be embodied by computer program instructions (software) that execute on the device 2500. Memory 2504 can also host one or more databases and can include one or more forms of volatile data storage media such as random-access memory (RAM), and/or one or more forms of non-volatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more computers, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth). One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network. A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user (such as a human annotator) to enter commands and information to device 2500, and also allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various processes and systems of present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable, and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer. Some of the methods and processes described above can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, general-purpose computer, special-purpose machine, virtual machine, software container, or appliance) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Some of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server over a communication network (e.g., the Internet).

While embodiments disclosed herein may be used in the oil, gas, hydrocarbon exploration or production environments, or in the production of other natural resources, such environments are merely illustrative. Systems, tools, assemblies, methods, devices, and other components of the present disclosure, or which would be appreciated in view of the disclosure herein, may be used in other applications and environments. In other embodiments, embodiments of the present disclosure may be used outside of a downhole environment, including in connection with the placement of utility lines, or in the automotive, aquatic, aerospace, hydro-electric, manufacturing, or telecommunications industries.

In the description herein, various relational terms may be used to facilitate an understanding of various aspects of some embodiments of the present disclosure. Relational terms such as "bottom," "below," "top," "above," "back," "front," "left," "right," "rear," "forward," "up," "down," "horizontal," "vertical," "clockwise," "counterclockwise," "upper," "lower," and the like, may be used to describe various components, including their operational or illus- trated position relative to one or more other components. Relational terms do not indicate a particular orientation for each embodiment within the scope of the description or claims, but are intended for convenience in facilitating reference to various components. Thus, such relational aspects may be reversed, flipped, rotated, moved in space, placed in a diagonal orientation or position, placed horizon-tally or vertically, or similarly modified.

Certain descriptions or designations of components as "first," "second," "third," and the like are also used to differentiate between identical components or between com-ponents which are similar in use, structure, or operation. Such language is not intended to limit a component to a singular designation or require multiple components. As such, a component referenced in the specification as the "first" component may be the same or different than a component that is referenced in the claims as a "first" component, and a claim may include a "first" component without requiring the existence of a "second" component.

Furthermore, while the description or claims may refer to "an additional" or "other" element, feature, aspect, compo-nent, or the like, it will not preclude there being a single element, or more than one, of the additional element. Where the claims or description refer to "a" or "an" element, such reference is not to be construed that there is just one of that element, but is instead to be inclusive of other components and understood as "at least one" of the element. It is to be understood that where the specification states that a com-ponent, feature, structure, function, or characteristic "may," "might," "can," or "could" be included, that particular component, feature, structure, or characteristic is provided in certain embodiments, but is optional for other embodi-ments of the present disclosure. The terms "couple," "coupled," "connect," "connection," "connected," "in con- nection with," and "connecting" refer to "in direct connec-tion with," or "in connection with via one or more interme-diate elements or members." Components that are "integral" or "integrally" formed include components made from the same piece of material, or sets of materials, such as by being commonly molded or cast from the same material, in the same molding or casting process, or commonly machined from the same piece of material stock. Components that are "integral" should also be understood to be "coupled" together.

Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encom-pass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

The terms "approximately," "about," and "substantially" as used herein represent an amount close to the stated amount that is within standard manufacturing or process tolerances, or which still performs a desired function or achieves a desired result. For example, the terms "approxi-mately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

Although various example embodiments have been described in detail herein, those skilled in the art will readily appreciate in view of the present disclosure that many modifications are possible in the example embodiments without materially departing from the present disclosure. Accordingly, any such modifications are intended to be included in the scope of this disclosure. Likewise, while the disclosure herein contains many specifics, these specifics should not be construed as limiting the scope of the disclo-sure or of any of the appended claims, but merely as providing information pertinent to one or more specific embodiments that may fall within the scope of the disclosure and the appended claims. Any described features from the various embodiments disclosed may be employed in com-bination.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited func-tion, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

What is claimed is:

1. A method for optimizing a drilling operation, the method comprising:

a) on a data processor, determining at least one fluid parameter for a drilling fluid and the drilling operation, wherein the at least one fluid parameter includes:

i) a first fluid parameter that relates to shear forces that break apart components of the drilling fluid during the drilling operation, ii) a second fluid parameter that characterizes mixing of drill cuttings with the drilling fluid during the drilling operation, wherein the second fluid parameter represents a dimensionless mixing number based on combination of a Froude number and a Shields number for the drilling fluid and the drill cuttings, and iii) a transport efficiency metric that characterizes transport of the drill cuttings by the drilling fluid during the drilling operation, wherein the transport efficiency metric is determined from the second fluid parameter in combination with a settling factor calculated from the first fluid parameter, wherein the settling factor is calculated from equations of the form:

$$L^* = \frac{L}{h} = u_0 \frac{9\eta(\dot{\gamma})d_a(M_n)}{2a^3(\rho_s - \rho_f)g},$$

$$d_a = 2(a + \delta)$$

$$d_a(Mn) = \begin{cases} 2\dfrac{a}{Mn}, & Mn < 1 \\ 2a, & Mn \geq 1 \end{cases}$$

where $u_0$ is derived from operational parameters of the drilling operation, $\gamma$ is derived from operational parameters of the drilling operation, $M_n$ is a Mason number for the drilling fluid and the drilling operation, $\alpha$ is a characteristic radius of the drill cuttings, $\delta$ is an accreted gel thickness, $\rho_s$ is a density of the drill cuttings, $\rho_f$ is a fluid density of the drilling fluid, and g is a gravitational constant;

b) performing multiple iterations of the determining of a) for varying drilling fluid formulations or varying operational parameters of the drilling operation and evaluating at least the transport efficiency metric of iii) for the multiple iterations to optimize a drilling fluid formulation for the drilling operation or at least one operational parameter of the drilling operation; and c) using the drilling fluid formulation or the at least one operational parameter optimized in b) in the drilling operation.

2. A method according to claim 1, wherein: the first fluid parameter represents the Mason number or a critical shear rate based on the Mason number.

3. A method according to claim 1, wherein: the first fluid parameter represents the Mason number, the Mason number based on a shear rate calculated from at least one operational parameter of the drilling operation selected from the group consisting of: drill pipe radius, drilled borehole radius, angular velocity of a drill string/drill bit, and drilling fluid flow rate.

4. A method according to claim 3, wherein: the drilling fluid comprises an oil-based mud; and the first fluid parameter represents the Mason number calculated from a mathematical equation of the form $$Mn = \frac{12\pi\eta_0\phi^2 G_{10}}{\sigma_y^2}\left(\frac{\varepsilon}{r}\right)\dot{\gamma},$$

where Mn is the Mason number, $\eta_0$ is a fluid viscosity of a continuous phase in the drilling fluid, $\Phi$ is a volume fraction of a dispersed phase in the drilling fluid, $G_{10}$ is a short time elastic modulus (at 10-second sample age) of the drilling fluid, $\sigma_y$ is a dynamic yield stress of the drilling fluid, $\varepsilon$ is a range of an interaction potential for the drilling fluid, r is a size of the dispersed phase in the drilling fluid, and $\gamma$ is the shear rate of the drilling fluid.

5. A method according to claim 3, wherein: the drilling fluid comprises a water-based mud; and the first fluid parameter represents the Mason number calculated from a mathematical equation of the form $$Mn = \frac{K\dot{\gamma}}{G},$$

where Mn is the Mason number,

K is a plastic viscosity of the drilling fluid,

G is a short time elastic modulus (at 10-second sample age) of the drilling fluid, and $\gamma$ is the shear rate of the drilling fluid.

6. A method according to claim 1, wherein: the drilling fluid comprises an oil-based mud; and the first fluid parameter represents a critical shear rate determined from flow curve measurements of the drilling fluid performed by an automated rheometer.

7. A method according to claim 1, wherein: the second fluid parameter represents a dimensionless mixing number calculated from a mathematical equation of the form $$\Xi = \left(\frac{\rho_f\omega R_i H}{n\eta}\sqrt{\frac{H}{R_i}} + 1\right)\frac{3}{2(\rho_s - \rho_f)ga}\eta\frac{R_i\omega}{H},$$

where E is the dimensionless mixing number based on the combination of a Froude number and a Shields number for the drilling fluid and the drill cuttings, $\rho_s$ is the characteristic density of the drill cuttings, $\rho_f$ is the fluid density of the drilling fluid, $\alpha$ is the characteristic radius of the drill cuttings, $R_i$ is a radius of a drilled borehole, $\omega$ is an angular velocity of a drill string/drill bit, $\eta$ is a viscosity of the drilling fluid at a desired shear rate, H is a gap between a drill pipe and the drilled borehole, g is the gravitational constant, and n is an arbitrary scale factor.

8. A method according to claim 1, wherein:

the at least one fluid parameter of a) further includes a third fluid parameter and a fourth fluid parameter that characterize normal stress in the drilling fluid during the drilling operation;

the third fluid parameter represents a first normal stress coefficient $\psi_1$ of the drilling fluid or an $N_1$ stress difference of the drilling fluid; and the fourth fluid parameter represents a second normal stress coefficient $\psi_2$ of the drilling fluid or an $N_2$ stress difference of the drilling fluid.

9. A method according to claim 1, wherein:

the evaluating of b) optimizes the drilling fluid formulation for the drilling operation by evaluating the transport efficiency metric of iii) for the varying drilling fluid formulations.

10. A method according to claim 9, wherein:

the varying drilling fluid formulations include one or more polymer additives.

11. A method according to claim 1, wherein:

the evaluating of b) optimizes the at least one operational parameter for the drilling operation by evaluating the transport efficiency metric of iii) for the varying operational parameters of the drilling operation.

12. A method according to claim 11, wherein:

the varying operational parameters of the drilling operation are selected from the group including drill bit/hole size, drill pipe size, drilling fluid flow rate, and/or rotational speed of a drill string.

\* \* \* \* \*